United States Patent
Steger et al.

(10) Patent No.: US 10,857,279 B2
(45) Date of Patent: Dec. 8, 2020

(54) DEVICE FOR EXTRACORPOREAL BLOOD TREATMENT WITH GRAVIMETRIC BALANCING AND POSSIBILITY OF ULTRAFILTRATION

(71) Applicant: B. BRAUN AVITUM AG, Melsungen (DE)

(72) Inventors: Jennifer Steger, Melsungen (DE); Markus Weiser, Breitenfurt (AT)

(73) Assignee: B. BRAUN AVITUM AG, Melsungen (DE)

( * ) Notice: Subject to any disclaimer, the term of this patent is extended or adjusted under 35 U.S.C. 154(b) by 109 days.

(21) Appl. No.: 16/175,108

(22) Filed: Oct. 30, 2018

(65) Prior Publication Data

US 2019/0134292 A1  May 9, 2019

(30) Foreign Application Priority Data

Nov. 7, 2017  (DE) ......................... 10 2017 125 962

(51) Int. Cl.
*A61M 1/16* (2006.01)
(52) U.S. Cl.
CPC ........ *A61M 1/1637* (2014.02); *A61M 1/1605* (2014.02); *A61M 1/1611* (2014.02);
(Continued)
(58) Field of Classification Search
CPC .............. A61M 1/1637; A61M 1/1635; A61M 1/1643; A61M 1/1647; A61M 1/1641
See application file for complete search history.

(56) References Cited

U.S. PATENT DOCUMENTS

| 4,197,196 A * | 4/1980 | Pinkerton ........... A61M 1/1656 210/321.65 |
| 4,728,433 A * | 3/1988 | Buck ....................... A61M 1/16 210/321.71 |

(Continued)

FOREIGN PATENT DOCUMENTS

| DE | 4122171 A1 | 1/1993 |
| EP | 0611228 A2 | 8/1994 |

(Continued)

OTHER PUBLICATIONS

German Search Report for German Application No. 10 2017 125 962.7, dated May 30, 2018, with English translation—17 pages.

(Continued)

*Primary Examiner* — Krishnan S Menon (57) ABSTRACT

A device for extracorporeal blood treatment, in particular a dialysis machine, including an internal fluidic system to which a blood treatment unit, in particular a dialyzer, can be connected, the internal fluidic system comprising at least one balancing chamber on the fresh flow side for balancing fresh treatment fluid flowing to the blood treatment unit and at least one balancing chamber on the used flow side for balancing used treatment fluid flowing off the blood treatment unit, wherein the device has a measuring device for gravimetric detection of treatment fluid in the balancing chamber on the fresh flow side and/or a measuring device for gravimetric detection of treatment fluid in the balancing chamber on the used flow side. A method of balancing treatment fluid in such a device.

10 Claims, 4 Drawing Sheets

(52) U.S. Cl.
CPC ........ *A61M 1/1635* (2014.02); *A61M 1/1641* (2014.02); *A61M 1/1643* (2014.02); *A61M 2205/332* (2013.01); *A61M 2205/3334* (2013.01); *A61M 2205/3337* (2013.01); *A61M 2205/3393* (2013.01); *A61M 2205/3396* (2013.01)

(56) References Cited

U.S. PATENT DOCUMENTS

| | | |
|---|---|---|
| 5,344,568 A | 9/1994 | Kitaevich et al. |
| 2008/0093276 A1* | 4/2008 | Roger ................... A61M 1/28 210/104 |
| 2013/0012914 A1 | 1/2013 | Burbank et al. |
| 2013/0292312 A1 | 11/2013 | Heide et al. |
| 2015/0060362 A1 | 3/2015 | Pouchoulin |
| 2017/0095604 A1* | 4/2017 | Cho ................... A61M 1/1649 |

FOREIGN PATENT DOCUMENTS

| | | |
|---|---|---|
| EP | 1684825 B1 | 1/2013 |
| WO | 2004069311 A1 | 8/2004 |
| WO | 2013164089 A1 | 11/2013 |

OTHER PUBLICATIONS

Extended European Search Report for European Application No. 18 204 411.5, dated Feb. 22, 2019, 15 pages.

* cited by examiner

DEVICE FOR EXTRACORPOREAL BLOOD TREATMENT WITH GRAVIMETRIC BALANCING AND POSSIBILITY OF ULTRAFILTRATION

CROSS REFERENCE TO RELATED APPLICATIONS

This application claims priority to German application DE 10 2017 125 962.7 filed Nov. 7, 2017, the contents of such application being incorporated by reference herein.

FIELD OF THE INVENTION

The invention relates to a device for extracorporeal blood treatment, in particular a dialysis machine, comprising an internal fluidic system to which a blood treatment unit, in particular a dialyzer, can be connected, wherein the internal fluidic system comprises at least one balancing chamber on the fresh flow side for balancing fresh treatment fluid flowing to the blood treatment unit and at least one balancing chamber on the used flow side for balancing used treatment fluid flowing off the blood treatment unit. It also relates to a method of balancing a treatment fluid in a device for extracorporeal blood treatment, in particular in a device according to aspects of the invention, the description or any of the attached claims, wherein fresh treatment fluid flowing to a blood treatment unit through an internal fluidic system of the device is balanced with a fresh flow-side balancing chamber of the internal fluidic system and used treatment fluid flowing off from the blood treatment unit is balanced with a used flow-side balancing chamber of the internal fluidic system and a deviation from a target balance or a misbalance is determined by comparing the fresh flow-side balance and the used flow-side balance.

BACKGROUND OF THE INVENTION

In dialysis technology, it is essential to balance the dialysis fluid on its way to the dialyzer and from the dialyzer to the drain. Therefore, dialysis machines comprising balancing means are used in today's dialysis applications. These balancing means monitor and ensure that a volume of liquid supplied to the dialyzer over a certain period of time corresponds to a volume of liquid removed from the dialyzer over the same period of time, i.e. the two volumes are exactly identical. In some applications, ultrafiltration, i.e. removal of liquid from the patient, may be desirable. In such a case, the ultrafiltration must also be exactly balanced, so that a precisely defined ultrafiltration volume is removed from the patient over the duration of a therapy. In summary, it can be said that a balancing procedure is used to monitor that no liquid or only exactly the intended quantity of liquid is withdrawn from the patient.

With known dialysis machines and procedures, an ultrafiltration volume withdrawn from the patient is not directly detected by the balancing device. In practice, particularly in balancing chamber systems provided with membranes, imbalances are caused by the system, for instance by varying pressure, varying temperature and varying volume flow rates within the balancing system. Balancing errors can, for example, lead to an undesired (additional) withdrawal of liquid by the balance chamber. In particular, changes in the back pressures affecting the balancing chambers can lead to incorrect balances and deviations in the (actual) fluid balance within the context of a dialysis treatment with known systems and procedures.

DESCRIPTION OF THE RELATED ART

Various methods and devices are prior art for balancing a dialysis fluid in the context of extracorporeal blood treatments (and possibly an ultrafiltration volume). For example, flow sensors (see, for example, WO 2013/164089), mass flow meters using the Coriolis effect, duplex pump technology, balancing chamber systems or gravimetric balancing systems in the form of bag scales (see, for example, DE 4122171 (A1) or EP 611228 B1) are known. Furthermore, balancing methods without balancing chambers but with membranes, for example with Coriolis measuring cells, or balancing methods with highly accurate, reciprocal pumps are known from prior art.

Figure 1:
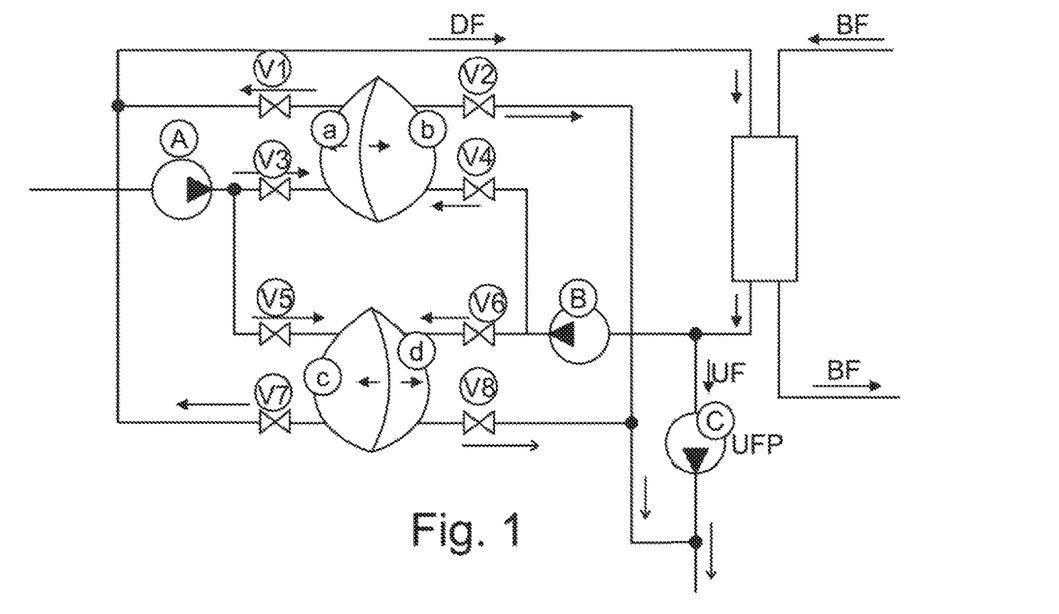
FIG. 1 shows a diagram of a detail of a known device for extracorporeal blood treatment.

A known balancing chamber system (see also diagram of FIG. 1), in which the treatment fluid conveyed by the system is balanced volumetrically, consists of two balancing chamber units, which are each divided by a movable diaphragm into four chambers (a, b, c, d). Two pumps (A, B) are used to fill the chambers a and c or b and d. A defined liquid removal rate (ultrafiltration rate) is forced with another pump C. The function of the system is divided into two phases.

In a first phase, the following initial condition exists: Chamber a is empty, chamber b is full (the membrane is far left in FIG. 1), chamber c is full, chamber d is empty (the membrane is far right in FIG. 1). The valves are switched as follows: V1 closed, V2 open, V3 open, V4 closed, V5 closed, V6 open, V7 open, V8 closed. The pump A fills chamber a through V3 with fresh dialysis fluid. As a result, the used dialysis fluid, which is located in chamber b, is led through V2 into the drain. Thus, pump B fills chamber d through V6 with used dialysis fluid. In this way, the fresh dialysis fluid in chamber c is pumped through V7 to the dialyzer.

In a second phase, the following initial conditions exist: Chamber b is empty, chamber a is full (the membrane is far right in FIG. 1), chamber d is full, chamber c is empty (the membrane is far left in FIG. 1). The valves are switched as follows: V1 open, V2 closed, V3 closed, V4 open, V5 open, V6 closed, V7 closed, V8 open. The pump A fills chamber c through V5 with fresh dialysis fluid. The used dialysis fluid, which is located in chamber d, is led through V8 into the drain. Thus, pump B fills chamber b through V4 with used dialysis fluid. In this way, the fresh dialysis fluid in chamber a is conveyed through V1 to the dialyzer.

To determine the exactness of the fluid balance, in particular the fluid withdrawal, the patient is weighed before and after completion of the therapy and conclusions are drawn about his fluid balance from any weight changes. With regard to the balance match, the disadvantage of the above known method and device is that due to the specific density, one liter of used dialysis fluid does not have a weight of one kilogram. A further complication is that the specific density of dialysis fluid depends on its exact composition, which means that used dialysis fluid has another density than fresh dialysis fluid. In addition, the density of used dialysis fluid is patient-specific and changes as blood purification progresses. However, in known volumetric processes it is widely assumed that one kilogram of used treatment fluid corresponds to a volume of about 1000 ml, which inevitably leads to ultrafiltration deviations. It is therefore fundamentally problematic to perform a balancing on the basis of conveyed/balanced volumes with weight changes of the patient.

Another disadvantage is that a volumetric method is usually sensitive to changes in pressure and/or temperature of the treatment fluid to be balanced:

For example, in a system described above, the treatment fluid cools down by a few degrees Celsius on its way from the balance chamber inlet side to the balance chamber outlet side. This increases the density of the treatment fluid and leads to balancing errors. Although ultrafiltration first depends on the performance of the ultrafiltration pump, balancing errors due to temperature conditions at the balancing chamber, in particular temperature differences between the inlet and outlet of the balancing chamber, can lead to an undesired (additional) extraction of liquid by the balancing chambers. Temperature changes or differences present there or elsewhere cause a change in the volume of the balanced liquid, which is caused by a change in the density of the liquid depending on the temperature, and thus lead to a misbalance.

In addition, the pressures on the balance chamber inlet side and the balance chamber outlet side usually differ. An increased pressure causes the balance chambers to expand and thus take up a slightly larger volume. In particular any changes in the default settings, such as the volume flow rate of the dialysis fluid, also known as DF flow, the blood-side pressure, etc., or dynamic pressure changes, for example due to aging of a DF filter or similar unit, can lead to pressure differences and thus to misbalances. The reason for this is that the pressure conditions in the system may change in accordance with the respective volume flow, possibly resulting in changes in volume which cannot be detected by the balancing device.

Another major disadvantage is that deviations may occur in balancing processes with volumetric methods due to air bubbles in the system. Finally, it is a disadvantage that in previously known volumetric processes, the withdrawal of liquid (ultrafiltration) is produced by a separate pump, which leads to complex blood treatment devices.

The above described lack of correlation between volume and weight is avoided by known gravimetric methods. In these methods, two bags (usually with a capacity of more than 10 liters) are attached to a hanging scale. One bag contains fresh dialysis fluid while the other bag is empty. During dialysis therapy, the fluid is pumped from one bag into the other. This reduces the weight of one bag and increases the weight of the other one. In sum, the weight of the two bags remains constant or increases in the event of a water removal rate (ultrafiltration). It is a major disadvantage that known gravimetric methods (weighing methods) only support a bag operation mode. Such methods can therefore only be used in the context of acute dialysis procedures.

Previously, a UF compensation factor has been stored in a control software to compensate for balancing errors. However, this compensation factor is independent of all the aforementioned variable parameters such as pressure, flow and temperature and thus represents only an "average compensation factor". Depending on the machine settings (deviations from default dialysis settings and default environmental parameters), this is more or less suitable and generally does not allow an exact compensation of UF errors.

In summary, it can be said that in the event of differences in pressure and/or temperature in the dialysis fluid, especially upstream and downstream of the balance chamber, misbalances can occur. Pressure differences can result from various reasons, such as changes in the DF flow, aging of components (wear of DF filters, blocking or deposition of disinfectants), differences in the temperature of the dialysis fluid relative to the ambient temperature of the dialysis machine, changes in the blood-side pressure, etc. Such misbalances therefore depend heavily on set parameters or parameters available on the machine as well as on external influencing factors.

SUMMARY OF THE INVENTION

Based on the prior art described above, the present invention is based on an object of eliminating the disadvantages mentioned above, in particular to form a device for extracorporeal blood treatment and a balancing method such that it is largely insensitive to changes in pressure and/or temperature and/or flow of the treatment fluid. In addition, a possibility is to be created to integrate ultrafiltration into the device and the process in an easy way. An integration of a degassing device and an air separator would be desirable. Finally, the invention is intended to reduce costs and simplify the treatment fluid cycle.

According to aspects of the invention, an object is achieved by a device for extracorporeal blood treatment, in particular a dialysis machine, comprising an internal fluidic system (fluid line system within the housing of a dialysis machine), to which a blood treatment unit, in particular a dialyzer, can be connected, the internal fluidic system comprising at least one balancing chamber on the fresh flow side for detecting/balancing fresh treatment fluid flowing to the blood treatment unit and at least one balancing chamber on the used flow side for detecting/balancing used treatment fluid flowing off the blood treatment unit, wherein the device has a measuring device for gravimetric detection, in particular for continuous gravimetric detection, of treatment fluid in the balancing chamber on the fresh flow side and/or a measuring device for gravimetric detection, in particular for continuous gravimetric detection, of treatment fluid in the balancing chamber on the used flow side.

With regard to the method, an object is achieved by a method of balancing treatment fluid in a device for extracorporeal blood treatment, in particular a device according to aspects of the invention, the description or any of the preceding claims, wherein fresh treatment fluid flowing to a blood treatment unit through an internal fluidic system of the device is detected/balanced with a balancing chamber on the fresh flow side of the internal fluidic system and used treatment fluid flowing off the blood treatment unit is detected/balanced with a balancing chamber on the used flow side of the internal fluidic system, and a deviation from the target balance and/or a misbalance is determined, in particular continuously detected/balanced, by comparing the balance on the fresh flow side and the balance on the used flow side, wherein treatment fluid present in the balancing chamber on the fresh flow side and/or treatment fluid present in the balancing chamber on the used flow side is gravimetrically detected with a measuring device.

A verification is performed by checking the patient's weight before and after blood treatment and determining a weight deviation. Through the invention, the detecting/balancing takes place directly gravimetrically, i.e. directly by detecting the weight of the treatment fluid. This has the great advantage over conventional devices and balances, which work or take place volumetrically and for which deviations can occur, as described above, since the weight of the volume to be balanced depends on the specific mass and the temperature of the medium, that fluid removal is directly linked to the weight of the patient and does not first have to be converted which is prone to errors.

A device according to aspects of the invention and a method according to aspects of the invention are particularly suitable for gravimetric balancing of a continuous flow of dialysis fluid. The scope of the invention also includes that the same device can gravimetrically measure/balance and calculate ultrafiltration and an ultrafiltration quantity without additional components.

Advantageous embodiments of the invention are claimed in the subclaims and are explained in more detail below.

One embodiment of the device is characterized in that the measuring device comprises a balance and/or a force sensor. This is particularly suitable and intended for an especially direct determination of the mass/weight of treatment fluid present in the balancing chamber. In another embodiment according to aspects of the invention, at least one weighing device, for example in the form of a scale or a force sensor as measuring device, can be located below and/or above the balancing chamber. The measuring device is used to determine the weight of the treatment fluid contained in the respective chamber. According to aspects of the invention, the measuring device may also be designed and arranged such that it can be used to determine the weight of the chamber and of the treatment fluid it contains. It is particularly advantageous if each balance chamber has such a measuring device associated to it, i.e. at least one weighing device/force sensor is located under each chamber. In this way, the mass/weight of the treatment fluid in each balancing chamber can be individually and directly detected and used for balancing.

According to a further embodiment, two balancing chambers can be arranged in each case on the fresh flow side and/or the used flow side of the treatment unit, in particular a first balancing chamber on the fresh flow side, a second balancing chamber on the fresh flow side, a first balancing chamber on the used flow side and a second balancing chamber on the used flow side. These can either be arranged fluidically parallel to or in series with each other and interconnected/connected to each other. In particular, according to aspects of the invention, the first balancing chamber on the fresh flow side and the second balancing chamber on the fresh flow side can be arranged/connected/interconnected with respect to each other in parallel or serially. Moreover, according to aspects of the invention, the first balancing chamber on the used flow side and the second balancing chamber on the used flow side can be arranged/connected/interconnected with respect to each other in parallel or serially. Gravimetric balancing is then carried out by the total of four separate chambers. In the context of the invention, for example, the respective chamber volume may range between 20 ml and 1500 ml, preferably amount to 100 ml. A larger chamber has the advantage of higher temperature stability and requires fewer switching cycles. A smaller chamber is more accurate in determining the balancing weight, but requires shorter switching cycles. The individual balancing chambers can be thermally insulated.

In the internal fluidic system, a valve, in particular a switchable shut-off valve or flow control valve, may be arranged on the inflow and/or outflow side of the balancing chamber, in particular of each of the balancing chambers, according to a further embodiment. Such a valve preferably has the two switching states "closed" and "open". The valves are designed in particular to control and/or regulate the inflow and/or outflow of treatment fluid to and/or from the balancing chamber. They can preferably be controlled automatically via a controller of the device.

In another embodiment according to aspects of the invention, at least one of the balancing chambers, preferably each balancing chamber, may have a ventilation opening. This ventilation opening may also be equipped in particular with a filter unit, such as a hydrophobic filter and/or a pressure relief valve. The advantage of the ventilation opening is that aeration can take place in the event of emptying and de-aeration in the event of filling the respective balancing chamber, so that there is no overpressure or underpressure against which the pumps must work, and the filling and emptying processes of the chamber can be carried out particularly quickly. In addition, air separating from the treatment fluid in the device during operation can be removed from the internal fluidic system through the ventilation opening. According to aspects of the invention, a de-aeration of the treatment fluid can take place in particular by forming a constriction in the flow cross-section in the internal fluidic system, in particular upstream of the first balancing chamber on the fresh flow side, which constriction is suitable and intended for generating a local negative pressure and degassing the treatment fluid. The constriction can be in the form of a throttle, especially in the form of an adjustable throttle.

In one embodiment of the invention the internal fluidic system comprises a pump for pumping treatment fluid on the inflow side of the balancing chamber and on the outflow side of the balancing chamber, in particular of each of the balancing chambers. In particular, the internal fluidic system may have a pump for pumping treatment fluid on both the inflow and outflow side of the fresh flow-side balancing chamber and on the inflow and outflow side of the used flow-side balancing chamber, i.e. a total of four pumps, namely a first fresh flow pump upstream of the balancing chamber(s) on the fresh flow side, a second fresh flow pump downstream of the balancing chamber(s) on the fresh flow side, a first used flow pump upstream of the balancing chamber(s) on the used flow side and a second used flow pump downstream of the balancing chamber(s) on the used flow side. Preferably, one valve, especially a switchable shut-off valve or flow control valve, is arranged between each pump and each balancing chamber in each case.

According to another embodiment of the invention, the balancing chamber or several or all balancing chambers can be designed as a piston-cylinder unit with the balancing chamber as a cylinder and a piston interacting with it and accommodated therein. According to one embodiment, the pistons are each driven by a motor, in particular by a linear motor, and can thus be moved up and down in the chamber and perform a conveying stroke. The pistons are guided on the wall of the chamber and sealed against it. Even in the case of balancing chambers designed as piston-cylinder units, their size within the scope of the invention is between approx. 20 ml and approx. 1500 ml, in particular approx. 100 ml. Balance chambers in the form of piston-cylinder units offer the advantage, among others, that the mass of the treatment fluid in the respective balance chamber can be better controlled. For example, if too much treatment fluid has been conveyed into one of the balancing chambers and its target weight has been exceeded, the linear motor can pump back part of the treatment fluid by operating in the opposite direction.

According to aspects of the invention, the treatment fluid in the respective balancing chamber can be continuously detected and in particular continuously balanced with the measuring device. In this way, it is advantageous to intervene in the method with a particularly simple regulating or controlling scheme.

Within the scope of the method according to aspects of the invention, in particular an undesirable deviation from a target balance or a misbalance can be compensated by generating an excess or reduced delivery of treatment fluid with a pump. In a further embodiment of the method according to aspects of the invention, a pump can be used to generate an excess or reduced delivery of treatment fluid in such a way that ultrafiltration is effected, i.e. such that liquid is extracted from a patient in a desired manner and to a desired degree. Due to the fact that the gravimetric detection of the treatment fluid in the respective balancing chamber achieves an unadulterated statement on its quantity (mass, weight), ultrafiltration can be controlled particularly easily and precisely, especially over the course of time.

According to aspects of the invention, especially in a first phase of the method, fresh treatment fluid on the fresh flow side can be conveyed into the first balancing chamber on the fresh flow side, whereas fresh treatment fluid is conveyed from the second balancing chamber on the fresh flow side to the treatment unit. In the meantime, used treatment fluid on the used flow side is conveyed from the treatment unit into the first balancing chamber on the used flow side, whereas used treatment fluid is conveyed from the second balancing chamber on the used flow side to a drain of the device. In a second phase of the method, fresh treatment fluid on the fresh flow side is conveyed into the second balancing chamber on the fresh flow side, whereas fresh treatment fluid is conveyed from the first balancing chamber on the fresh flow side to the treatment unit. On the used flow side, used treatment fluid is conveyed from the treatment unit into the second balancing chamber on the used flow side, whereas used treatment fluid is conveyed from the first balancing chamber on the used flow side to a drain of the device. In this embodiment, the first and second balancing chambers on the fresh flow side as well as the first and second balancing chambers on the used flow side are each arranged parallel to one another/fluidically connected to one another.

In an alternative embodiment, in a first phase of the method, fresh treatment fluid on the fresh flow side is conveyed into the first balancing chamber on the fresh flow side, whereas fresh treatment fluid from the second balancing chamber on the fresh flow side is conveyed to the treatment unit. At the same time, used treatment fluid on the used flow side is conveyed from the treatment unit into the first balancing chamber on the used flow side, and used treatment fluid is conveyed from the second balancing chamber on the used flow side to a drain of the device. In this first phase, the first and second balancing chambers on the fresh flow side as well as the first and second balancing chambers on the used flow side are decoupled from one another in terms of fluidics, for example with an intermediate shut-off valve. In a second phase of the method, fresh treatment fluid on the fresh flow side is conveyed from the first balancing chamber on the fresh flow side into the second balancing chamber on the fresh flow side. Simultaneously, fresh treatment fluid from the second balancing chamber on the fresh flow side can be conveyed to the treatment unit. On the used flow side, used treatment fluid is conveyed from the treatment unit into the first balancing chamber on the used flow side. At the same time, used treatment fluid can also be conveyed from the second balancing chamber on the used flow side to an outlet of the device. In this second phase of the process, the first and second balancing chambers on the fresh flow side as well as the first and second balancing chambers on the used flow side are fluidically coupled to one another, for example by switching on the intermediate shut-off valve. In this embodiment, the first and second balancing chambers on the fresh flow side as well as the first and second balancing chambers on the used flow side are serially arranged/fluidically connected to each other.

In summary, it can be said that in particular the following advantages and improvements can be achieved through the invention:

The device and the method according to aspects of the invention are particularly suitable for gravimetric continuous balancing and for balancing a continuous flow.

The device and the method according to aspects of the invention are particularly suitable for balancing an ultrafiltration quantity without requiring an autonomous separate ultrafiltration pump.

The balancing is robust against changes in terms of pressure and/or flow and/or temperature of the treatment fluid.

For correct balancing it is no longer necessary that the pressure on the respective input and output sides of the balancing chambers is constant and/or identical or must be maintained to be constant and/or identical.

The device and the method according to aspects of the invention are particularly suitable for both the implementation of degassing (water inlet) and the implementation of an air separator (dialyzer outlet), so that no independent, separate degassing pump and/or air separator is required.

The device and the method according to aspects of the invention are particularly robust against balancing errors caused by air bubbles.

The device and the method according to aspects of the invention are particularly suitable for a self-test or matching. Two balancing chambers on the fresh flow side can be tested or adjusted, for example, by setting different filling levels/quantities therein with pumps, stopping the pumps and opening all fresh flow side chamber valves. For example, two balancing chambers on the used flow side can be tested or matched by setting different filling levels/quantities therein with pumps, stopping the pumps and opening all the chamber valves on the used flow side. Via the opened chamber valves, equal levels and thus equal filling quantities (weight) will occur in the respective balancing chambers. In the context of the invention, a possibility for a self-test or a matching of a balancing chamber on the fresh flow side with a balancing chamber on the used flow side can take place by filling the balancing chamber on the fresh flow side with a certain quantity of treatment fluid and emptying the balancing chamber on the used flow side to a certain residual quantity of treatment fluid. Afterwards, treatment fluid is pumped from the balancing chamber on the fresh flow side into the balancing chamber on the used flow side. Since only a residual quantity of treatment fluid corresponding to the residual quantity in the balancing chamber on the used flow side at the beginning of the matching is contained in the balancing chamber on the fresh flow side, the weight of the treatment fluid in the balancing chamber on the used flow side must have increased to the initial weight of the balancing chamber on the fresh flow side.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 2:
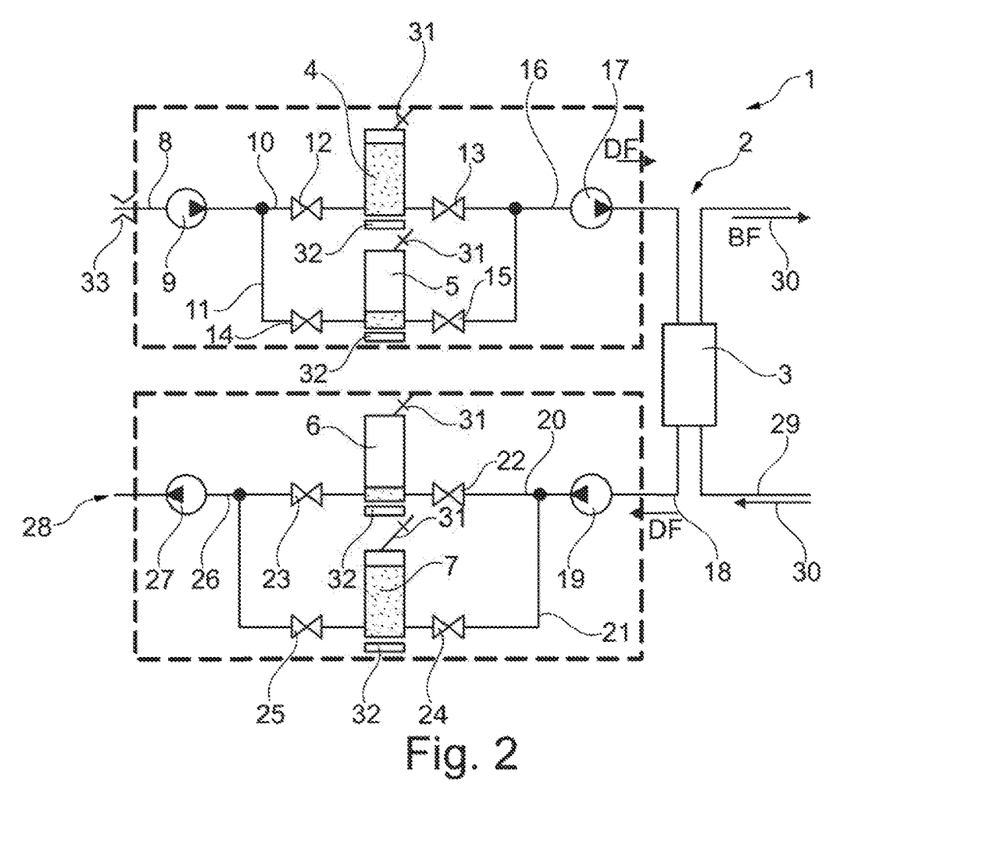
FIG. 2 shows a diagram of a section forming a balancing unit of a first embodiment of a device according to aspects of the invention for extracorporeal blood treatment.

FIG. 2 schematically shows a detail of a first embodiment of a device 1 according to aspects of the invention for extracorporeal blood treatment. In the present example, the device 1 is designed as dialysis machine 1 and comprises an internal fluidic system 2 to which a blood treatment unit 3, in this case a dialyzer 3, can be connected. The internal fluidic system 2 comprises a first balancing chamber 4 on the fresh flow side and a second balancing chamber 5 on the fresh flow side, each for balancing fresh treatment fluid flowing to the blood treatment unit 3. It also comprises a first balancing chamber 6 on the used flow side and a second balancing chamber 7 on the used flow side, each for balancing the used treatment fluid flowing off the blood treatment unit 3. The individual balancing chambers 4, 5, 6, 7 may be thermally insulated.

On the fresh flow side, the internal fluidic system 2 comprises an inflow line 8 connected to a (not shown) reservoir for fresh treatment fluid. A first fresh flow pump 9 is arranged in said inflow line in the internal fluidic system 2. Downstream of the pump 9, the line 8 is divided into a first fresh flow line branch 10 and a second fresh flow line branch 11, which are realized so as to be fluidically parallel to each other.

In the first fresh flow line branch 10, a valve 12 is arranged upstream of the first balancing chamber 4 on the fresh flow side and a valve 13 is arranged downstream of the first balancing chamber 4 on the fresh flow side. In the second fresh flow line branch 11, a valve 14 is arranged upstream of the second balancing chamber 5 on the fresh flow side and a valve 15 is arranged downstream of the second balancing chamber 5 on the fresh flow side. Downstream of the two valves 13, 15, the first fresh flow line branch 10 and the second fresh flow line branch 11 merge again to form a fresh flow line 16, in the further course of which a second fresh flow pump 17 is arranged and which is finally connected to the dialyzer 3 as treatment unit 3.

On the used flow side, the internal fluidic system 2 has a used flow line 18 which is fluidically connected to the dialyzer 3. A first used flow pump 19 is arranged in said used flow line. Downstream of the first used flow pump 19, the used flow line 18 is divided into a first used flow line branch 20 and a second used flow line branch 21, which are realized so as to be fluidically parallel to each other.

In the first used flow line branch 20, a valve 22 is arranged upstream of the first balancing chamber 6 on the used flow side and a valve 23 is arranged downstream of the first balancing chamber 6 on the used flow side. In the second used flow line branch 21, a valve 24 is arranged upstream of the second balancing chamber 7 on the used flow side and a valve 25 is arranged downstream of the second balancing chamber 7 on the used flow side. Downstream of the two valves 23, 25, the first used flow line branch 20 and the second used flow line branch 21 merge again to form a used flow line 26, in the further course of which a second used flow pump 27 is arranged and which is finally connected via a drain 28 to a (not shown) reservoir for used treatment fluid.

FIG. 2 also shows a part of an extracorporeal blood line 29 with indicated blood flow direction 30.

The device of FIG. 2 uses a total of four chambers 4, 5, 6 and 7, each of which may be thermally insulated. The switching rate of the chambers 4, 5, 6, 7 depends on the respective volumes of the chambers. As indicated in FIG. 2, the first fresh flow line 10, the second fresh flow line 11, the first used flow line branch 20 and the second used flow line branch 21 are connected to the respective chamber 4, 5, 6, 7 as close to the bottom as possible, so that as few dead spaces as possible remain within the respective chamber 4, 5, 6, 7 in which treatment fluid can accumulate.

Each of the four chambers 4, 5, 6, 7 has a ventilation opening 31, in the present case located at the top of the respective chamber 4, 5, 6, 7. The ventilation opening 31 serves to equalize the pressure when filling and emptying the respective chamber 4, 5, 6, 7. The ventilation opening 31 may be provided with a hydrophobic filter not shown in the Figure.

Below each individual chamber 4, 5, 6, 7 there is a measuring device 32 in the form of a scale or weighing device 32. Alternatively, the measuring device 32 can be arranged above the respective chamber 4, 5, 6, 7. The measuring device 32 is suitable and intended to continuously determine the weight of the respective chamber 4, 5, 6, 7 which are filled with more or less treatment fluid. The determined weights can be used to ascertain the mass flow of the pumps 9, 17, 19, 27. This is also used to determine the filling level of the chambers 4, 5, 6, 7.

To ensure a continuous flow of treatment fluid, its delivery is divided into two phases. At the beginning of a first phase, the chambers 4, 5, 6, 7 each having a respective filling volume of 100 ml are filled with the following masses of treatment fluid:

Chamber 4: 20 g, chamber 5: 80 g, chamber 6: 20 g, chamber 7: 80 g.

In the first phase, the device 1 is operated as follows:

Pump 9 fills chamber 4 through valve 12. Valve 12 is open, valve 13 is closed.

Pump 17 empties chamber 5 through valve 15. Valve 14 is closed, valve 15 is open.

Pump 19 fills chamber 6 through valve 22. Valve 23 is closed, valve 22 is open.

Pump 27 empties chamber 7 through valve 25. Valve 25 is open, valve 24 is closed.

The operation in the first phase continues until the chambers 4, 5, 6, 7 have reached a full or empty state.

At the beginning of a second phase, the chambers 4, 5, 6, 7 each having a respective filling volume of 100 ml are filled with the following masses of treatment fluid:

Chamber 4: 80 g, chamber 5: 20 g, chamber 6: 80 g, chamber 7: 20 g

In the second phase, the device 1 is operated as follows:

Pump 9 fills chamber 5 through valve 14. Valve 14 is open, valve 15 is closed.

Pump 17 empties chamber 4 through valve 13. Valve 12 is closed, valve 13 is open.

Pump 19 fills chamber 7 through valve 24. Valve 25 is closed, valve 24 is open.

Pump 27 empties chamber 6 through valve 23. Valve 23 is open, valve 22 is closed.

The operation in the second phase also continues until the chambers 4, 5, 6, 7 have reached a full or empty state.

As soon as the respective switching point (empty or full) of a chamber 4, 5, 6, 7 has been reached, the two valves belonging to a chamber 4, 5, 6, 7 close. As soon as all valves of all chambers 4, 5, 6, 7 are closed, the next phase begins, i.e. after the first phase the second phase, then again the first phase and so on.

The device of FIG. 2 can also be operated in an ultrafiltration mode within the scope of the invention, i.e. in such a way that liquid is withdrawn from a patient in a desired manner and to a desired degree. To generate ultrafiltration, the upper switching points of the chambers 4, 5, 6, 7 are defined differently and the fresh flow pump 17 and the used flow pump 19 are operated at different flow rates. In the present example, the fresh flow pump 17 runs at a flow rate of 500 g/min, which flow rate is determined by the measuring device. The used flow pump 19 is operated with a different delivery rate of 510 g/min, resulting in a total ultrafiltration of 600 g/h. At such conveying rates, the switching points 20 g and 80 g result for the chambers 4 and 5 (corresponding to a displacement of 60 g at 8.33 strokes per minute). For the chambers 6 and 7, the switching points are 20 g and 81.2 g (corresponding to a displacement of 61.2 g at 8.33 strokes per minute).

The fresh flow pump 9 and the used flow pump 27 must each be operated in such a way that the chambers fluidically connected to them are filled or emptied at least as quickly as the fresh flow pump 7 and the used flow pump 19 need in order to empty or fill the respectively other chamber fluidically connected to them.

In addition, the device of the embodiment of FIG. 2 is designed for degassing the treatment fluid. A constriction 33 or throttle 33 is arranged in the inflow line 8, which generates a dynamic negative pressure in the treatment fluid flowing through it. As a result of the negative pressure present there, any air dissolved in the treatment fluid separates in the form of air bubbles, which can then escape through the ventilation openings 31 in the balancing chamber 4 or 5. Air in the form of air bubbles that penetrate into the system, e.g. through leaks at the dialyzer couplings, can easily be removed from the internal fluidic system via the balancing chambers 6 and 7 with the device 1 according to aspects of the invention. Advantageously, a separate air separator for this purpose is not required for the device 1 of the invention.

A matching of the balancing chambers 4 and 5 or 6 and 7 is particularly easy with the device 1 according to aspects of the invention. Via the pumps 9, 17, 19, 27, different filling levels/filling quantities are set in the balancing chambers 4, 5, 6, 7, for example 20 g, 50 g and 80 g. Then the pumps 9, 17, 19, 27 are stopped and all chamber valves 12, 13, 14, 15 and 22, 23, 24, 25 are opened. Via the opened chamber valves 12, 13, 14, 15 and 22, 23, 24, 25, equal levels and thus equal filling quantities (weight) appear in the balancing chambers 4 and 5 or 6 and 7.

In addition, the balancing chambers 4 to 6 (or 4 to 7, 5 to 6, 5 to 7) can be easily matched as follows: Via the pumps 9, 17, 19, 27, the balancing chamber 4 is filled (e.g. with 80 g treatment fluid) and the balancing chamber 6 is emptied (e.g. to a quantity of 20 g treatment fluid). The treatment fluid is then pumped from the balancing chamber 4 into the balancing chamber 6. This can be done in a first variant with only one pump by bridging one of the pumps 17 and 19 with a bypass not shown in FIG. 2, so that the remaining pump 17 or 19 directly produces a flow between the balancing chambers 4 and 6. Alternatively, this can be done in a second variant with two pumps by operating the pumps 17 and 19 in such a way that both have the same delivery rate. For this purpose, for example, a pressure sensor not shown in FIG. 2 can be used between the two pumps 17 and 19. If the pumps 17 and 19 are then operated at such a speed that this pressure does not change, it is ensured that both pumps 17 and 19 convey the same amount of treatment fluid. After the lower level of 20 g treatment fluid has been reached in the balancing chamber 4, the weight of the treatment fluid in the balancing chamber 6 must have increased to the initial weight of the balancing chamber 4, i.e. 80 g in this case.

Finally, the device 1 according to aspects of the invention enables a simultaneous matching of all balancing chambers 4, 5, 6, 7. By integrating a short-circuit valve (not shown in FIG. 2) between e.g. the valves 14 and 15, the above described matching procedure can be carried out simultaneously for all balancing chambers 4, 5, 6, 7.

In an embodiment according to aspects of the invention, the measurement results can be secured with a two-channel measurement. This can be done, for example, by carrying out an additional differential measurement between the respective balancing chambers before and after the dialyzer 3 by weighing the chambers (e.g. chamber 4 with chamber 6 and chamber 5 with chamber 7), in particular with the aid of a rocker device not shown in the Figures, on which the corresponding chambers are mounted. Alternatively, the total weight of two chambers, e.g. of the chambers 4 and 6 and the chambers 5 and 7, can be determined on a scale likewise not shown in the Figures, and the results of the individual scales can be compared by forming a difference.

Figure 3:
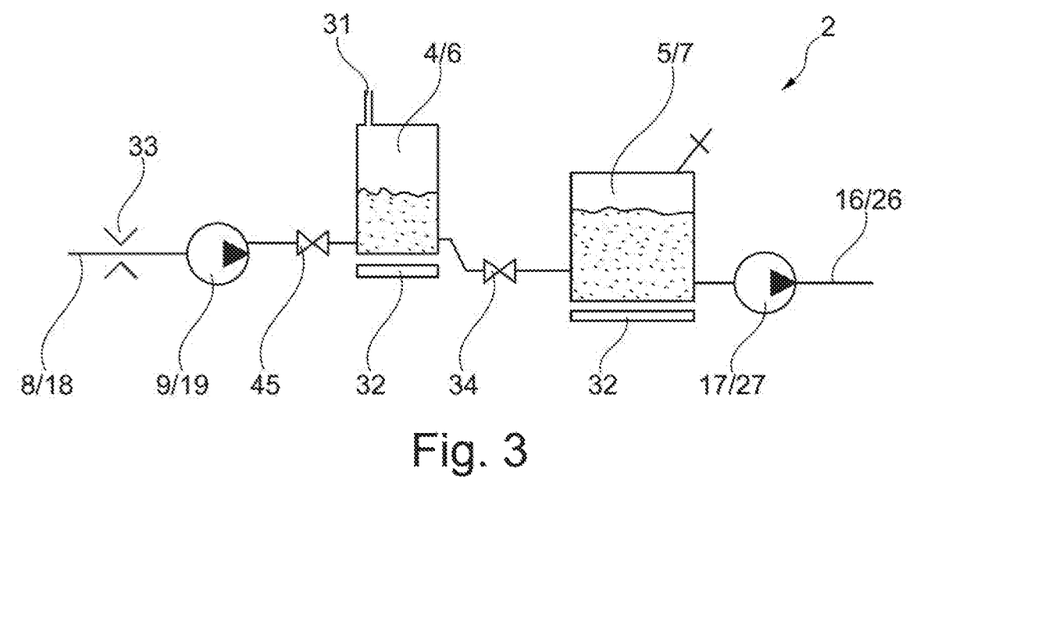
FIG. 3 shows a diagram of a section forming a balancing unit of a second embodiment of a device according to aspects of the invention for extracorporeal blood treatment.

FIGS. 2 and 3 can be used to illustrate a second embodiment variant of the invention. The second embodiment differs from the first embodiment shown in FIG. 2 in that the components in FIG. 2 within the dashed borders are replaced by the components shown in FIG. 3. In particular the balancing chambers 4, 5, 6, 7 are identical in both embodiments. In the following description of the second embodiment, only the fresh flow side of the device 1 is described and it is pointed out that the used flow side of the device is designed accordingly and modified compared to the first embodiment of FIG. 2.

In this embodiment of the device 1, the balancing chambers 4 and 5 or 6 and 7 are not parallel to each other but arranged in series. The balancing chambers 5 and 6 have approximately double or more than double the volume of the chambers 4 and 7 arranged in series with them. On the fresh flow side, the fresh flow pump 17 continuously pumps treatment fluid from the second balancing chamber 5 through the dialyzer 3. The measuring device 32 or alternatively a flow sensor can be used to determine the (mass) flow caused by this pump 17. The first balancing chamber 4 on the fresh flow side is used for the actual balancing. The weight of the treatment fluid present in it is continuously measured by the measuring device 32 located below the chamber 4. The first balancing chamber 4 on the fresh flow side has, similar to the first embodiment of FIG. 2, two switching points, namely empty (e.g. 20 g) and full (e.g. 80 g). If the balancing chamber 4 is empty (i.e. contains only 20 g liquid), the valve 45 opens while the valve 34 closes, so that the first fresh flow pump 9 fills the first balancing chamber 4 on the fresh flow side. Since the ventilation opening 31 of balancing chamber 4 is then closed, any air in the chamber 4 is compressed and the pressure in the chamber 4 increases. As soon as the first balancing chamber 4 on the fresh flow side is full (i.e. contains 80 g treatment fluid), the valve 45 closes and the valve 34 opens. The pressure built up in the first balancing chamber 4 on the fresh flow side (or due to a height difference which may exist between chambers 4 and 5) causes treatment fluid to flow from the first balancing chamber 4 on the fresh flow side into the second balancing chamber 5 on the fresh flow side. As soon as the first chamber 4 is empty (i.e. contains only 20 g treatment fluid), the valve 34 closes and the valve 45 opens and the cycle starts again. If it is ensured that treatment fluid flows from the first balancing chamber 4 on the fresh flow side into the second balancing chamber 5 on the fresh flow side to a sufficient extent or at a sufficient frequency, it is never completely drained. Thus, the pump 17 can provide a continuous flow through the dialyzer 3. It should be noted that only the measuring device 32 under the first balancing chamber 4, 6 is sufficient for balancing.

The device 1 according to the second embodiment is also suitable for degassing and set up for creating a negative pressure in the treatment fluid by a constriction 33 in the internal fluidic system 2, here in front of the fresh flow pump 9. Any air bubbles generated thereby will accumulate in the first balancing chamber 4 on the fresh flow side, resulting in an increase in pressure. This increases the outflow speed of the treatment fluid from the balancing chamber 4 into the balancing chamber 5. To avoid excessive pressures in the chamber 4, it is equipped with a pressure relief valve arranged in the ventilation opening 31 and not shown in FIG. 3.

Compared to the first embodiment (FIG. 2), the second embodiment of the invention has the advantage that fewer valves are required. However, the chamber volume of the chambers 5 and 7 is larger than that of the first embodiment and the third embodiment described below.

Figure 4:
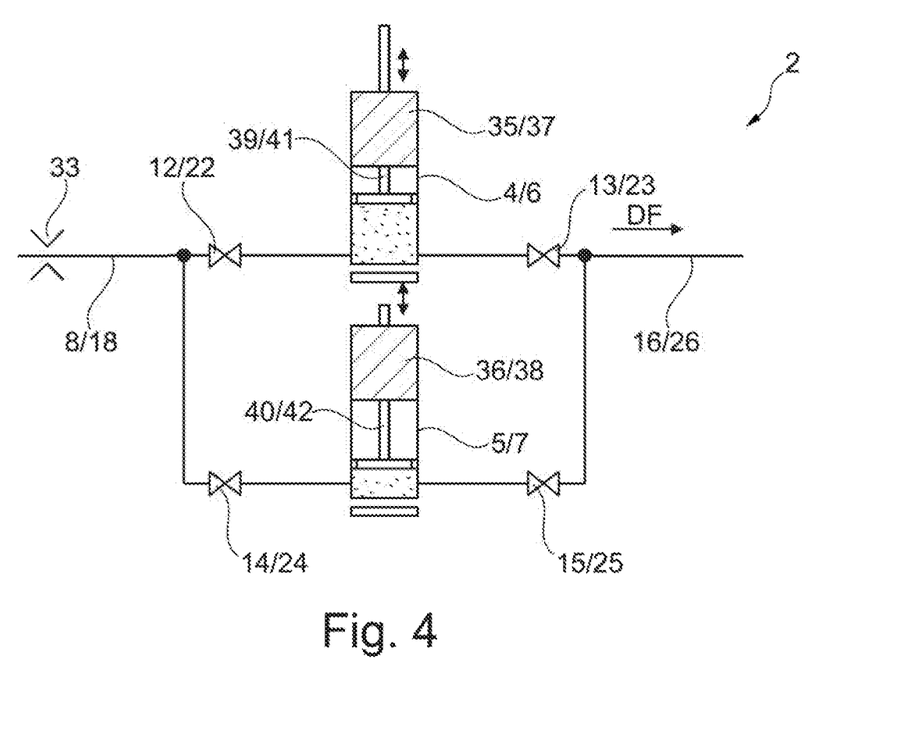
FIG. 4 shows a diagram of a section forming a balancing unit of a third embodiment of a device according to aspects of the invention for extracorporeal blood treatment.

FIGS. 2 and 4 can be used to illustrate a third embodiment variant of the invention. The third embodiment differs from the first embodiment shown in FIG. 2 in that the components in FIG. 2 within the dashed borders are replaced by the components shown in FIG. 4. In the following description of the third embodiment, only the fresh flow side of the device 1 is described and it is pointed out that the used flow side of the device is designed accordingly and modified compared to the first embodiment of FIG. 2.

Compared to the first embodiment, their pumps 9, 17, 19 and 27 are replaced by correspondingly arranged linear motors 35, 36, 37, 38. The linear motors 35, 36, 37, 38 interact with pistons 39, 40, 41, 42 movably arranged in the corresponding balancing chambers 4, 5, 6, 7. The pistons 39, 40, 41, 42 are guided in the respective chamber 4, 5, 6, 7 and sealed against the chamber wall, so that the chambers 4, 5, 6, 7 each form a cylinder belonging to the respective piston 39, 40, 41, 42. The chambers 4, 5, 6, 7 are filled and emptied with a movement of the pistons 39, 40, 41, 42 therein caused by the linear motors 35, 36, 37, 38. The pistons can be arranged either hanging or standing within the scope of the invention. The individual balancing chambers 4, 5, 6, 7 may be thermally insulated. Within the scope of the invention, their size is between approx. 20 ml to approx. 1500 ml.

Depending on the size of the chambers 4, 5, 6, 7, the switching cycle of the pistons 39, 40, 41, 42 changes.

The third embodiment shown in FIG. 4 has the advantage over the first embodiment shown in FIG. 2 that the mass of the treatment fluid in the respective chamber 4, 5, 6, 7 can be better adjusted. If the target weight is exceeded, i.e. there is too much treatment fluid in the respective chamber 4, 5, 6, 7, the linear motor 35, 36, 37, 38 can pump back part of the treatment fluid. A disadvantage compared to the first embodiment is that venting of chambers 4, 5, 6, 7 is not possible, each linear motor 35, 36, 37, 38 and the associated piston 39, 40, 41, 42 are additionally weighed during balancing by the measuring device 32 and the gravity pressure (hydrostatic pressure) is not decoupled and is therefore also measured by measuring device 2.

Figure 5:
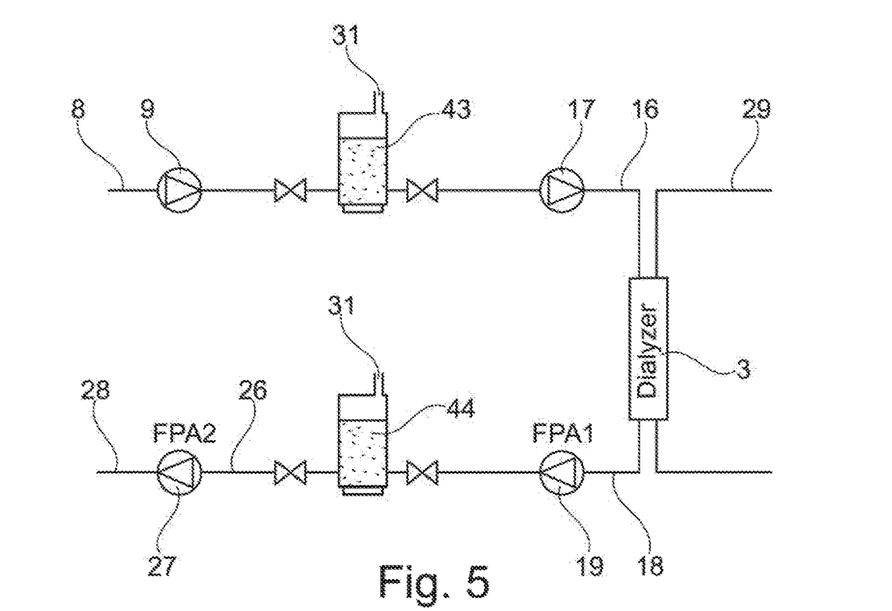
FIG. 5 shows a diagram of a section forming a balancing unit of a fourth embodiment of a device according to aspects of the invention for extracorporeal blood treatment.

A fourth embodiment of device 1 according to aspects of the invention is shown in FIG. 5. On the fresh flow side (upstream of dialyzer 3), there is only one (single) balancing chamber 43 on the fresh flow side, and on the used flow side (downstream of the dialyzer 3) there is only one (single) used flow side balancing chamber 44. The first fresh flow pump 9 fills the balancing chamber 43 on the fresh flow side very quickly (e.g. with 10 times the dialysate flow). When the filling process is completed, the second fresh flow pump 17 delivers treatment fluid from balancing chamber 43 at a constant rate until the chamber 43 is empty. In the same way, the first used flow pump 19 fills the balancing chamber 44 on the used flow side with a constant flow rate. When the balancing chamber 44 is full, the second used flow pump 27 empties the chamber 44 with a high flow rate (e.g. 10 times the flow rate). In this way, a quasi-continuous dialysate flow is generated particularly easily. The cycle repeats itself periodically. Measurement and balancing are carried out in the same way as for the embodiments described above.

Figure 6:
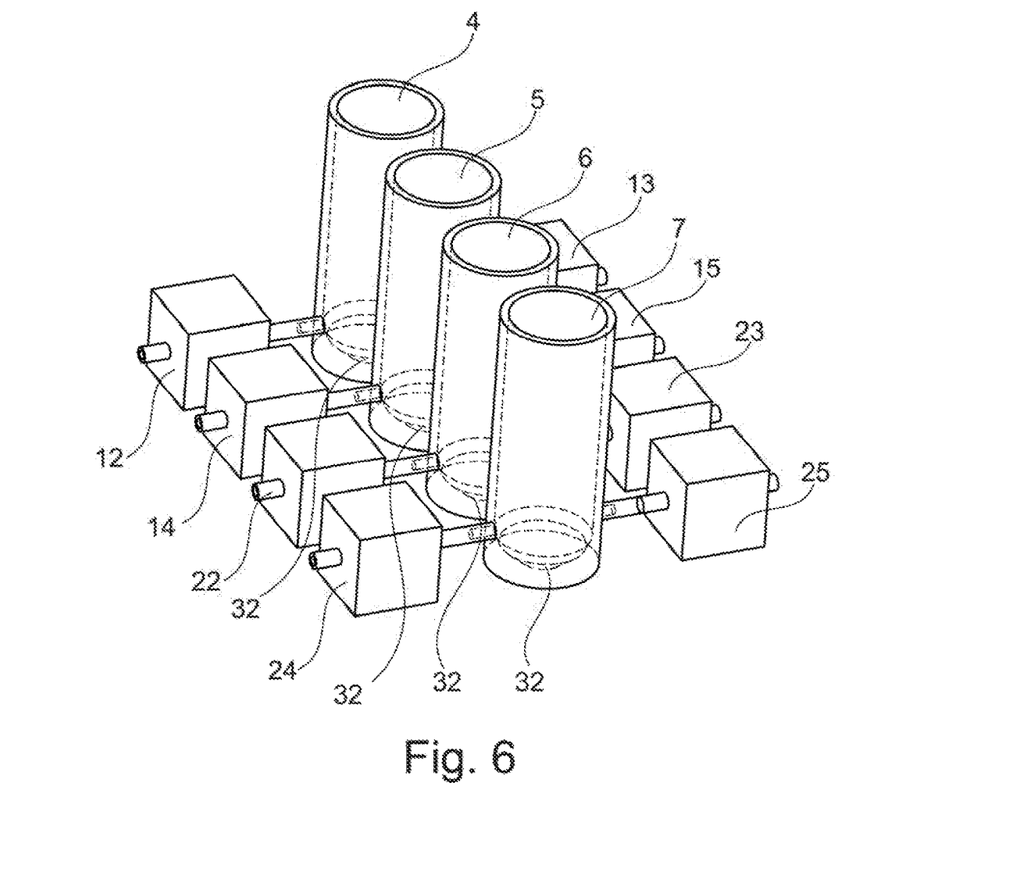
FIG. 6 shows a schematic perspective illustration of a balancing unit of an embodiment of a device according to aspects of the invention for extracorporeal blood treatment.
Figure 7:
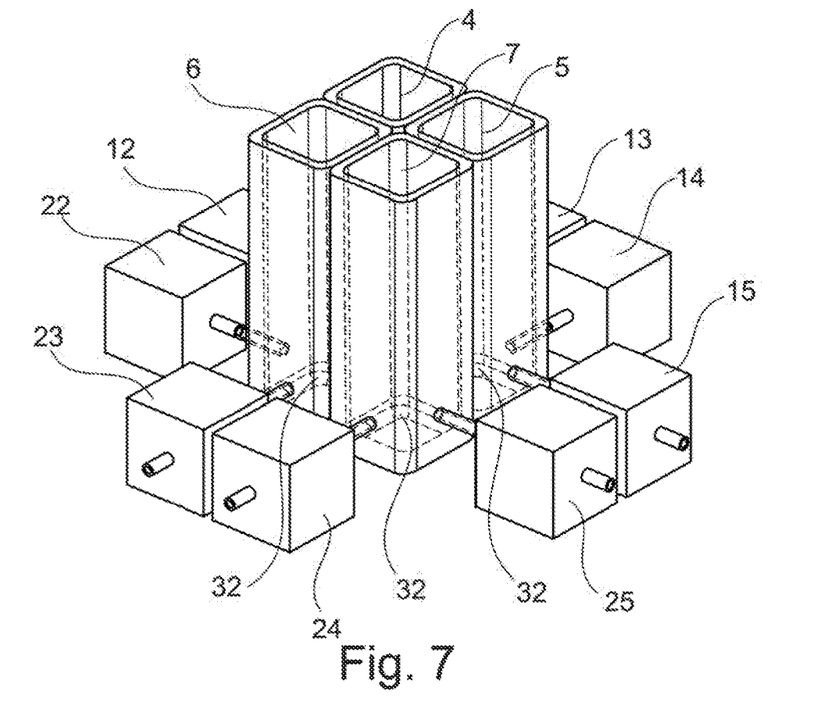
FIG. 7 shows a schematic perspective illustration of a balancing unit of an embodiment of a device according to aspects of the invention for extracorporeal blood treatment.

FIGS. 6 and 7 show possible configurations of the first and second embodiments of the invention. These are four separate chambers 4, 5, 6, 7, under each of which a measuring device 32 is installed. The valves 12, 13, 14, 15 and 22, 23, 24, 25 are mounted separately from the chambers 4, 5, 6, 7 in both exemplary embodiments in order to decouple the chambers 4, 5, 6, 7 as far as possible in mechanical terms. For example, switching process of the valves are not transferred directly to the measuring devices 32, here in the form of force sensors 32.

All chambers 4, 5, 6, 7 are illustrated with open top, but they are provided with a cover (not shown in FIGS. 6 and 7) having an overflow connection and/or a hydrophobic filter, for example.

Figure 8:
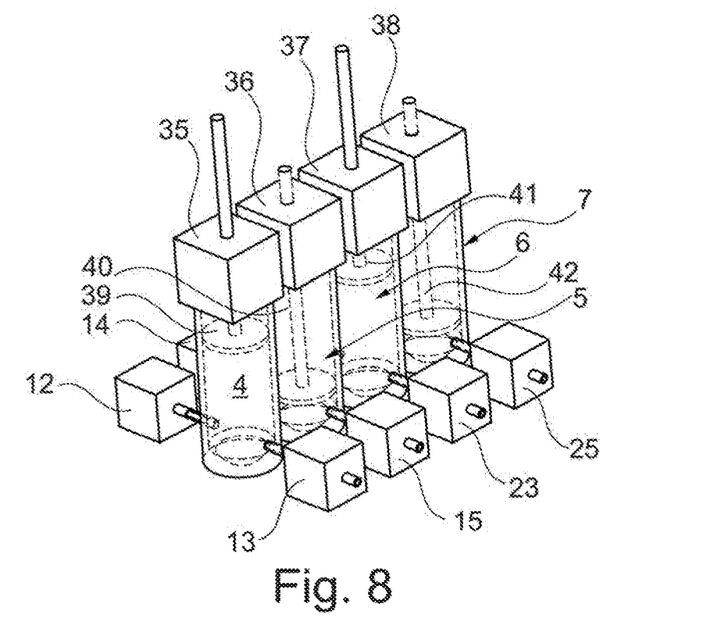
FIG. 8 shows a schematic perspective illustration of a balancing unit of an embodiment of a device according to aspects of the invention for extracorporeal blood treatment.

Finally, FIG. 8 shows a possible implementation of the third embodiment. This is based on the implementation shown in FIG. 6. The chambers 4, 5, 6, 7 were supplemented by the linear motors 35, 36, 37, 38. These move each one of the pistons 39, 40, 41, 42 up and down in the respective chamber 4, 5, 6, 7, providing the desired flow of treatment fluid.

The invention claimed is:

1. A device for extracorporeal blood treatment comprising:
   an internal fluidic system to which a blood treatment unit can be connected, wherein the internal fluidic system comprises:
   a first balancing chamber and a second balancing chamber on a fresh flow side for balancing fresh treatment fluid flowing to the blood treatment unit; and
   a third balancing chamber and a fourth balancing chamber on a used flow side for balancing used treatment fluid flowing off the blood treatment unit, a first measuring device for gravimetric detection of the fresh treatment fluid in the first balancing chamber and a second measuring device for gravimetric detection of the fresh treatment fluid in the second balancing chambers on the fresh flow side, and a third measuring device for gravimetric detection of the used treatment fluid in the third balancing chamber and a fourth measuring device for gravimetric detection of the used treatment fluid in the fourth balancing chambers on the used flow side.

2. The device according to claim 1, wherein the at least one measuring device comprises at least one of a balance and a force sensor to determine the mass of treatment fluid present in the balancing chamber.

3. The device according to claim 1, wherein the first and second balancing chambers are fluidically arranged in parallel.

4. The device according to claim 1, wherein a switchable shut-off valve is arranged in the internal fluidic system on at least one of the inflow side and the outflow side of each balancing chamber for at least one of controlling and regulating the inflow and the outflow of the treatment fluid.

5. A device for extracorporeal blood treatment comprising:

an internal fluidic system to which a blood treatment unit can be connected, wherein the internal fluidic system comprises:

a first balancing chamber and a second balancing chamber on a fresh flow side for balancing fresh treatment fluid flowing to the blood treatment unit; and a third balancing chamber and a fourth balancing chamber on a used flow side for balancing used treatment fluid flowing off the blood treatment unit, at least one measuring device for gravimetric detection of treatment fluid in at least one of the first and second balancing chambers on the fresh flow side, and at least one measuring device for gravimetric detection of treatment fluid in at least one of the third and fourth balancing chambers on the used flow side;

wherein at least one of the balancing chambers has a ventilation opening having a filter unit.

6. The device according to claim 1, wherein the internal fluidic system comprises a pump for pumping treatment fluid on the inflow side of each balancing chamber and on the outflow side of each balancing chamber.

7. A device for extracorporeal blood treatment comprising:

an internal fluidic system to which a blood treatment unit can be connected, wherein the internal fluidic system comprises:

a first balancing chamber and a second balancing chamber on a fresh flow side for balancing fresh treatment fluid flowing to the blood treatment unit; and a third balancing chamber and a fourth balancing chamber on a used flow side for balancing used treatment fluid flowing off the blood treatment unit, at least one measuring device for gravimetric detection of treatment fluid in at least one of the first and second balancing chambers on the fresh flow side, and at least one measuring device for gravimetric detection of treatment fluid in at least one of the third and fourth balancing chambers on the used flow side;

wherein each balancing chamber is configured as a piston-cylinder unit with a cylinder and a piston cooperating with the cylinder and accommodated therein.

8. The device according to claim 1, wherein a constriction in the flow cross-section is formed in the internal fluidic system upstream of the first and second balancing chambers on the fresh flow side for generating a local negative pressure and degassing the treatment fluid.

9. The device for extracorporeal blood treatment of claim 1, wherein the device is a dialysis machine and the blood treatment unit is a dialyzer.

10. The device according to claim 1, wherein the third and fourth balancing chambers are fluidically arranged in parallel.

* * * * *